(12) United States Patent
Medina et al.

(10) Patent No.: US 10,420,794 B2
(45) Date of Patent: *Sep. 24, 2019

(54) POLYSACCHARIDE PARTICLE MIXTURE

(71) Applicant: Medtronic, Inc., Minneapolis, MN (US)

(72) Inventors: Jennifer G. Medina, Jacksonville, FL (US); James Britton Hissong, Jacksonville, FL (US); Matthew F. Myntti, St. Augustine, FL (US); Dana A. Oliver, Jacksonville, FL (US); Brian J. Vaccaro, Athens, GA (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/389,430

(22) Filed: Dec. 22, 2016

(65) Prior Publication Data

US 2017/0100427 A1    Apr. 13, 2017

Related U.S. Application Data

(63) Continuation of application No. 14/324,889, filed on Jul. 7, 2014, now Pat. No. 9,561,248, which is a continuation of application No. 12/429,127, filed on Apr. 23, 2009, now Pat. No. 8,802,652.

(60) Provisional application No. 61/047,580, filed on Apr. 24, 2008.

(51) Int. Cl.
| | |
|---|---|
| *A61K 31/722* | (2006.01) |
| *A61K 9/00* | (2006.01) |
| *A61K 47/38* | (2006.01) |
| *A61L 27/20* | (2006.01) |
| *A61L 27/26* | (2006.01) |
| *A61L 27/56* | (2006.01) |
| *C08B 15/00* | (2006.01) |
| *C08B 37/08* | (2006.01) |
| *C08B 37/00* | (2006.01) |
| *C08L 1/28* | (2006.01) |
| *C08L 5/08* | (2006.01) |
| *A61K 31/717* | (2006.01) |
| *A61K 31/718* | (2006.01) |
| *A61K 31/045* | (2006.01) |
| *A61K 47/36* | (2006.01) |
| *A61L 2/08* | (2006.01) |
| *C08J 3/12* | (2006.01) |
| *A61L 2/00* | (2006.01) |
| *A61K 9/06* | (2006.01) |
| *A61L 27/52* | (2006.01) |

(52) U.S. Cl.
CPC .......... *A61K 31/722* (2013.01); *A61K 9/0019* (2013.01); *A61K 9/0024* (2013.01); *A61K 9/0043* (2013.01); *A61K 9/06* (2013.01); *A61K 31/045* (2013.01); *A61K 31/717* (2013.01); *A61K 31/718* (2013.01); *A61K 47/36* (2013.01); *A61K 47/38* (2013.01); *A61L 2/007* (2013.01); *A61L 2/081* (2013.01); *A61L 2/087* (2013.01); *A61L 27/20* (2013.01); *A61L 27/26* (2013.01); *A61L 27/52* (2013.01); *A61L 27/56* (2013.01); *C08B 15/005* (2013.01); *C08B 37/003* (2013.01); *C08B 37/0042* (2013.01); *C08J 3/124* (2013.01); *C08L 1/286* (2013.01); *C08L 5/08* (2013.01); *A61K 9/0046* (2013.01); *A61K 9/0085* (2013.01); *A61L 2300/404* (2013.01); *A61L 2400/06* (2013.01); *C08G 2210/00* (2013.01)

(58) Field of Classification Search
CPC .. A61K 31/722; A61K 31/718; A61K 31/717; A61K 31/045; A61K 9/0024; A61K 47/36; A61K 47/38; C08L 5/08; C08L 1/286; C08B 37/003; C08B 15/005; A61L 27/26; A61L 27/20
See application file for complete search history.

(56) References Cited

U.S. PATENT DOCUMENTS

| | | | |
|---|---|---|---|
| 3,184,385 | A | 5/1965 | Anderson |
| 3,678,931 | A | 7/1972 | Cohen |
| 3,914,214 | A | 10/1975 | Trimnell et al. |
| 3,989,044 | A | 11/1976 | Meierhoefer |

(Continued)

FOREIGN PATENT DOCUMENTS

| | | |
|---|---|---|
| CA | 2 348 842 A1 | 5/2000 |
| CA | 2 574 232 | 1/2006 |

(Continued)

OTHER PUBLICATIONS

Fwu-Long et al., pH-sensitive behavior of two-component hydrogels composed of N,O-carboxymethal chitosan and alginate, J. Biomater, Sci. Polymer Edn., vol. 16, No. 11, 1333-1345 (2005).

(Continued)

*Primary Examiner* — Jonathan S Lau
(74) *Attorney, Agent, or Firm* — Patterson Thuente Pedersen, P.A.

(57) ABSTRACT

Tissue and other body structures may be protected using a dry, free-flowing, sterilized mixture of chitosan particles and oxidized polysaccharide particles in sealed packaging. The mixture may assist in returning an injured, inflamed or surgically repaired surface to a normal state, e.g., through one or more healing mechanisms such as modulation of an inflammatory response, phagocytosis, mucosal remodeling, reciliation or other full or partial restoration of normal function.

19 Claims, 5 Drawing Sheets

(56) References Cited

U.S. PATENT DOCUMENTS

| | | | |
|---|---|---|---|
| 4,604,384 A | 8/1986 | Smith et al. | |
| 4,659,700 A | 4/1987 | Jackson | |
| 4,895,724 A | 1/1990 | Cardinal et al. | |
| 4,960,413 A | 10/1990 | Sagar et al. | |
| 4,983,385 A | 1/1991 | Hasegawa et al. | |
| 5,308,546 A | 5/1994 | Hansen et al. | |
| 5,312,324 A | 5/1994 | Walthour | |
| 5,318,780 A | 6/1994 | Viegas et al. | |
| 5,550,189 A | 8/1996 | Qin et al. | |
| 5,623,064 A | 4/1997 | Vournakis et al. | |
| 5,667,778 A | 9/1997 | Atala | |
| 5,676,964 A | 10/1997 | Della Valle et al. | |
| 5,679,658 A | 10/1997 | Elson | |
| 5,688,522 A | 11/1997 | Hardy | |
| 5,723,144 A | 3/1998 | Hardy | |
| 5,747,475 A | 5/1998 | Nordquist et al. | |
| 5,770,712 A | 6/1998 | Roy et al. | |
| 5,820,608 A | 10/1998 | Luzio et al. | |
| 5,836,970 A * | 11/1998 | Pandit | A61L 15/225 606/213 |
| 5,840,341 A | 11/1998 | Watts et al. | |
| 5,993,846 A | 11/1999 | Friedman et al. | |
| 6,051,648 A | 4/2000 | Rhee et al. | |
| 6,096,018 A | 8/2000 | Luzio et al. | |
| 6,123,965 A | 9/2000 | Jacob et al. | |
| 6,224,893 B1 | 5/2001 | Langer et al. | |
| 6,290,712 B1 | 9/2001 | Nordquist et al. | |
| 6,320,029 B1 | 11/2001 | Miekka et al. | |
| 6,334,968 B1 | 1/2002 | Shapiro et al. | |
| 6,342,251 B1 | 1/2002 | Illum et al. | |
| 6,344,488 B1 | 2/2002 | Chenite et al. | |
| 6,346,272 B1 | 2/2002 | Viegas et al. | |
| 6,417,347 B1 | 7/2002 | Herrmann et al. | |
| 6,458,889 B1 | 10/2002 | Trollsas et al. | |
| 6,514,522 B2 | 2/2003 | Domb | |
| 6,545,042 B2 | 4/2003 | Sung et al. | |
| 6,566,406 B1 | 5/2003 | Pathak et al. | |
| 6,599,627 B2 | 7/2003 | Yeo et al. | |
| 6,602,952 B1 | 8/2003 | Bentley et al. | |
| 6,632,423 B2 | 10/2003 | Jafari et al. | |
| 6,664,301 B1 | 12/2003 | Kross | |
| 6,706,690 B2 | 3/2004 | Reich et al. | |
| 6,719,987 B2 | 4/2004 | Burrell et al. | |
| 6,806,260 B1 | 10/2004 | Hirofumi et al. | |
| 6,809,085 B1 | 10/2004 | Elson et al. | |
| 6,835,389 B1 | 12/2004 | Dohi et al. | |
| 6,989,373 B2 | 1/2006 | Des Rosiers | |
| 6,991,652 B2 | 1/2006 | Burg | |
| 7,053,068 B2 | 5/2006 | Prinz | |
| 7,070,582 B2 | 7/2006 | Freyman et al. | |
| 7,087,249 B2 | 8/2006 | Burrell et al. | |
| 7,098,194 B2 | 8/2006 | Chenite et al. | |
| 7,125,860 B1 | 10/2006 | Renier et al. | |
| 7,195,675 B2 | 3/2007 | Okazaki et al. | |
| 7,229,966 B2 | 6/2007 | Quay et al. | |
| 7,354,600 B1 | 4/2008 | Bernkop-Schnürch | |
| 7,727,547 B2 | 6/2010 | Fortune et al. | |
| 7,834,065 B2 | 11/2010 | Nakajima et al. | |
| 8,802,652 B2 | 8/2014 | Myntti et al. | |
| 9,561,248 B2 | 2/2017 | Myntti et al. | |
| 2002/0042473 A1 | 4/2002 | Trollsas et al. | |
| 2002/0064580 A1 | 5/2002 | Gord et al. | |
| 2002/0193812 A1 | 12/2002 | Patel et al. | |
| 2003/0073663 A1 | 4/2003 | Wiseman et al. | |
| 2004/0029855 A1 | 2/2004 | Klaveness et al. | |
| 2004/0101548 A1 * | 5/2004 | Pendharkar | A61L 15/28 424/445 |
| 2004/0127698 A1 | 7/2004 | Tsai et al. | |
| 2004/0137041 A1 | 7/2004 | You | |
| 2004/0157734 A1 * | 8/2004 | Mertens | A61L 15/60 502/401 |
| 2004/0176477 A1 * | 9/2004 | Davison | A01N 43/16 516/77 |
| 2004/0219117 A1 | 11/2004 | Shibata | |
| 2005/0002893 A1 | 1/2005 | Goldmann | |
| 2005/0019404 A1 | 1/2005 | Sung et al. | |
| 2005/0069572 A1 | 3/2005 | Williams et al. | |
| 2005/0096282 A1 | 5/2005 | Lewin et al. | |
| 2005/0136122 A1 | 6/2005 | Sadozai et al. | |
| 2005/0176620 A1 | 8/2005 | Prestwych et al. | |
| 2005/0208122 A1 | 9/2005 | Allen et al. | |
| 2005/0238702 A1 | 10/2005 | Ishihara et al. | |
| 2005/0284809 A1 * | 12/2005 | Looney | A61L 24/0036 210/502.1 |
| 2006/0054634 A1 | 3/2006 | Mekata | |
| 2006/0134185 A1 | 6/2006 | Odermatt et al. | |
| 2006/0147539 A1 | 7/2006 | Sung et al. | |
| 2006/0172000 A1 | 8/2006 | Cullen et al. | |
| 2006/0234871 A1 | 10/2006 | Dalrymple et al. | |
| 2006/0292030 A1 | 12/2006 | Odermatt et al. | |
| 2007/0020314 A1 | 1/2007 | Haro et al. | |
| 2007/0031467 A1 | 2/2007 | Abrahams et al. | |
| 2007/0031474 A1 | 2/2007 | Tayot | |
| 2007/0048291 A1 | 3/2007 | Mang et al. | |
| 2007/0066924 A1 | 3/2007 | Hopman et al. | |
| 2007/0087059 A1 | 4/2007 | Everaerts et al. | |
| 2007/0098675 A1 | 5/2007 | Elisseff et al. | |
| 2007/0110788 A1 | 5/2007 | Hissong et al. | |
| 2007/0191963 A1 | 8/2007 | Winterbottom et al. | |
| 2007/0202142 A1 | 8/2007 | Laugier et al. | |
| 2007/0243130 A1 | 10/2007 | Chen et al. | |
| 2007/0243131 A1 | 10/2007 | Chen et al. | |
| 2007/0264310 A1 | 11/2007 | Hissong et al. | |
| 2008/0031854 A1 | 2/2008 | Prestwich et al. | |
| 2008/0069857 A1 | 3/2008 | Yeo et al. | |
| 2008/0075657 A1 | 3/2008 | Abrahams | |
| 2008/0317765 A1 | 12/2008 | Izraeli et al. | |
| 2008/0319101 A1 | 12/2008 | Nakajima et al. | |
| 2009/0005339 A1 | 1/2009 | Scholz et al. | |
| 2009/0010982 A1 | 1/2009 | Abrahams et al. | |
| 2009/0016978 A1 | 1/2009 | Courtois | |
| 2009/0041814 A1 | 2/2009 | Nanbu | |
| 2009/0062233 A1 | 3/2009 | Ji et al. | |
| 2009/0270346 A1 * | 10/2009 | Tijsma | A61K 9/0043 514/55 |
| 2010/0291055 A1 | 11/2010 | Athanasiadis et al. | |

FOREIGN PATENT DOCUMENTS

| | | |
|---|---|---|
| CN | 1872351 A | 12/2006 |
| EP | 0 815 879 A2 | 1/1998 |
| EP | 1 228 771 A1 | 8/2002 |
| EP | 1 880 738 A1 | 1/2008 |
| FR | 2 889 449 A1 | 8/2005 |
| JP | H07-116241 | 9/1995 |
| JP | 2000-095678 | 4/2000 |
| JP | 2002-327338 | 11/2002 |
| JP | 2008-247975 | 10/2008 |
| JP | 2008-285611 | 11/2008 |
| TO | WO 2009/028965 A1 | 3/2009 |
| WO | WO 92/16245 | 10/1992 |
| WO | WO 93/21906 | 11/1993 |
| WO | WO 96/14828 | 5/1996 |
| WO | WO 98/19718 | 5/1998 |
| WO | WO 98/31712 A2 | 7/1998 |
| WO | WO 99/01166 | 1/1999 |
| WO | WO 99/07416 | 2/1999 |
| WO | WO 00/40252 | 7/2000 |
| WO | WO 01/00246 A2 | 1/2001 |
| WO | WO 03/020771 A1 | 3/2003 |
| WO | WO 03/057274 A2 | 7/2003 |
| WO | WO 03/080135 A1 | 10/2003 |
| WO | WO 2004/026200 A | 4/2004 |
| WO | WO 2006/080523 A1 | 8/2006 |
| WO | WO 2007/059390 A1 | 5/2007 |
| WO | WO 2007/071375 A | 6/2007 |
| WO | WO 2008/005671 A2 | 1/2008 |
| WO | WO 2008/008857 A | 1/2008 |
| WO | WO 2008/067655 A | 6/2008 |
| WO | WO 2008/097317 A | 8/2008 |

(56) References Cited

FOREIGN PATENT DOCUMENTS

OTHER PUBLICATIONS

Fwu-Long et al., Synthesis and characterization of biodegradable TPP/genipin co-crosslinked chitosan gel beads, Polymer, 44, 6521-6530 (2003).
Reyes et al., A Modified Chondroitin Sulfate Aldehyde Adhesive for Sealing Corneal Incisions, Investigative Ophthalmology & Visual Science, vol. 6, No. 4, 1247-1250 (Apr. 2005).
Mi et al., Synthesis and Characterization of a Novel Chitosan-Based Network Prepared Using Naturally-Occurring Crosslinker, J Polym Sci, Part A: Polym Chem, 38, 2804-2814 (2000).
Mi et al., Synthesis and characterization of biodegradable TPP/ genipin co-crosslinked chitosan gel beads, Polymer, 44, 6521-30 (2003).
Roldo et al., Mucoadhesive thiolated chitosans as platforms for oral controlled drug delivery: synthesis and in vitro evaluation, European Journal of Pharmaceutics and Biopharmaceutics, 57, 115-121 (2004).
Krauland et al., Viscoelastic Properties of a New in situ Gelling Thiolated Chitosan Conjugate, Drug Development and Industrial Pharmacy, 31, 885-893 (2005).
Bernkop-Schnürch, Thiomers: A new generation of mucoadhesive polymers, Advanced Drug Delivery Reviews, 57, 1569-1582 (2005).
Bernkop-Schnürch et al., Thiomers: Preparation and in vitro evaluation of a mucoadhesive nanoparticulate drug delivery system, International journal of Pharmaceutics, 317, 76-81 (2006).
Weng et al., Rheological Characterization of in Situ Crosslinkable Hydrogels Formulated from Oxidized Dextran and N-Carboxyethyl Chitosan, Biomacromolecules, 8, 1109-1115 (2007).
Wang et al., Multifunctional chondroitin sulphate for cartilage tissue-biomaterial integration, nature materials, vol. 6, 385-392 (May 2007).
Aspden et al, Chitosan as a Nasal Delivery System: The Effect of Chitsan on In Vitro and In Vivo Mucociliary Transport Rates in Human Turbinates and Volunteers, J Pharm Sci, 86, 4, 509-513 (1997).
Costain et al., Prevention of postsurgical adhesions with N,O-carboxymethyl chitosan: Examination of the most efficacious preparation and the effect of N,O-carboxymethyl chitosan on postsurgical healing, Surgery, 121, 3, 314-319 (1997).
Hong et al., Covalently crosslinked chitosan hydrogel: Properties of in vitro degradation and chondrocyte encapsulation, Acta Biomaterialia, 3, 1, 23-31 (2007).
Park et al., Crosslinked hydrogels for tympanic membrane repair, Otolaryngology—Head and Neck Surgery, 135, 887-883 (2006).
Carlsson et al., Immobilization of Urease by Thiol-Disulphide Interchange with Concomitant Purification, Eur. J. Biochem, 44, 189-194 (1974).
Hoober et al., Sulfhydryl Oxidase from Egg White, The Journal of Biological Chemistry, vol. 274, No. 32, Issue of Aug. 6, 22147-22150 (1999).
Barbucci et al., Hyaluronic acid hydrogel in the treatment of osteoarthritis, Biomaterials 23, 4503-4513 (2002).
Anonymous, "CHITOFLEX™—Surgical", Sep. 2007,2 pages, retrieved from the Internet at: www.alltracel.com/Portals/1/ChitoFlex%20-%20Surgical%20Product%20Overview%20Brochure.pdf.
Szczubialka et al., "Novel drug carrier—Chitosan gel microspheres with covalently attached nicotinic acid", Journal of Controlled Release, Elsevier, vol. 16, No. 2, e13-e15, XP005794286 (2006).
Mwale Fackson at al., "Biological evaluation of chitosan salts cross-linked to genipin as a cell scaffold for disk tissue engineering", Tissue Engineering, vol. 11, No. 1-2, 130-140, XP002518499 (2005).
Bernkop-Schnürch, A., et al., "Improvement in the mucoadhesive properties of alginate by the covalent attachment of cysteine", Journal of Controlled Release, Elsevier, 71, 277-285 (2001).
Athanasiadis, Theo et al., "Effects of a novel chitosan gel on mucosal wound healing following endoscopic sinus surgery in a sheep model of chronic rhinosinusitis", The Laryngoscope, vol. 118, No. 6, 1088-1094, XP002535403 (2008).
NovaMatrix Ultrapure Biopolymer Systems Catalog and prices, 4 pp. (Sep. 2011).
NovaMatrix Ultrapure Biopolymer Systems, "Chitosan", Data Sheets, 2 pp. (2011).
Higashiyama, Takanobu, "Novel functions and applications of trehalose*", Pure Appl. Chem., vol. 74, No. 7, pp. 1263-1269 (2002).
Kumar et al., "Chitosan Chemistry and Pharmaceutical Perspectives", Chem. Rev. 104, pp. 6017-6084 (2004).
Bernkop-Schnürch, A., et al.,"Thiolated polymers-thiomers: synthesis and in vitro evaluation of chitosan-2-iminothiolane conjugates", Int'l Journal of Pharmaceutics, vol. 260, Issue 2, Jul. 24, 2003.
Wang, et. al, "The synthesis and characterization of novel bioadhesive material thiolated chitosan", Chemical Journal of Chinese Universities, No. 1, vol. 29, January, pp. 206-211 (2008).
Haugh, M.G. et al., "The effect of dehydrothermal treatment on the mechanical and structural properties of collagen-GAG scaffolds", Royal College of Surgeons in Ireland, Department of Anatomy, 23 pages, (2009).
Ringe, K. et al., "Nanoparticle Drug Delivery to the Brain", Encyclopedia of Nanoscience and Nanotechnology, vol. 7, pp. 91-104, (2004).
Definition of derivative, retrieved from Merriam-Webster online dictionary at: http://www.merriamwebster.com/dictionary/derivative on Apr. 6, 2011, 2 pages.
Moura, M.J. et al., "Rheological study of genipin cross-linked chitosan hydrogels", Biomacromolecules, 8(12), pp. 3823-3829 (2007).
Huang et al., "The Application and Development of New Crosslinking Agent Genipin in Biomedicine", Shanghai biomedical Engineering Journal, No. 1, vol. 24, pp. 21-25 (2003).
Liu, G. et al., "Synthesis and Characterization of Chitosan/Dextran-Based Hydrogels for Surgical Use", Macromol. Symp., 279, pp. 151-157, (2009).
Leitner et al., "Thiomers in noninvasive polypeptide delivery: In vitro and in vivo characterization of a polycarbophilcysteine/glutathione gel formulation for human growth hormone", J. Pharm. Sci, 93, 1682-1691 (2004).
Bromberg, "Intelligent Polyelectrolytes and Gels in Oral Drug Delivery" Department of Chemical Engineering, Massachusetts Institute of Technology, Cambridge, Massachusetts, U.S.A. in Current Pharmaceutical Biotechnology, 4, 339-349 (2003).
Prestwich et al., "3-D culture in synthetic extracellular matrices: New tissue models for drug toxicology and cancer drug delivery", Advances in Enzyme Regulation, Elsevier Ltd., 47, 196-207 (2007).
Kast et al., "Thiolated polymers-thiomers: development and in vitro evaluation of chitosan-thioglycolic acid conjugates", Biomaterials, Elsevier Science Publishers, 22, 2345-2352 (2001).
Ex parte Robert S. Bray, Appeal No. 2011-013427 in U.S. Appl. No. 11/686,054 (BPAI 2013).
Novamatrix, by FMC Biopolymer, retrieved from internet on Jul. 5, 2012 at: http://www.novamatrix.biz/Portals/novamatrix/Content/Docs/ProductDocs/chitosan_General_info.pdf, published in 2011, 2 pages.
Grabovac et al., "Comparison of the mucoadhesive properties of various polymers", Advanced Drug Delivery Review, vol. 57, pp. 1713-1723 (2005).
Grillet et al., "Polymer Gel Rheology and Adhesion", Chapter 3, Polymer Gel Rheology and Adhesion, 23 pages, (2012), downloaded from: http://www.intechopen.com/books/rheology/rheology-and-adhesion-of-polymer-gels.
Bernkop-Schnürch et al., "Thiolated chitosans", European Journal of Pharmaceutics Biopharmaceutics, vol. 57, pp. 9-17 (2004).
G. Sandri et al., "Mucoadhesive and penetration enhancement properties of three grades if hyaluronic acid using porcine buccal and vaginal tissue, Caco-2 cell lines, and rat jejunum." Journal of Pharmacy and Pharmacology, vol. 56, pp. 1083-1090 (2004).
A Subramanian, HY Lin. (Crosslinked chitosan: Its physical properties and the effects of matrix stiffness on chondrocyte cell mor-

(56) References Cited

OTHER PUBLICATIONS phology and proliferation. Journal of Biomedical Research Part A, vol. 75A, Issue 3, pp. 742-753 (Aug. 18, 2005).

Kim, J.H. M.D. et al., "Antiadhesive effect of the mixed solution of sodium hyaluronate and sodium carboxymethylcellulose after endoscopic sinus surgery", American Journal of Rhinology, vol. 21, No. 1, pp. 95-99, additional copyright page (Jan.-Feb. 2007).

Laffleur, F. Hintzen et al., Enzymatic degradation of thiolated chitosan, Drug development and industrial pharmacy 39(10) pp. 1531-1539 (2013).

Definition of gel, IUPAC Gold Book, http://goldbook.iupac.org/G02600.html, accessed online on Jul. 15, 2016.

Struszczyk, H.J., et al., "Microcrystalline Chitosan. I. Preparation and Properties of Microcrystalline Chitosan", Journal of Applied Polymer Science, vol. 33, pp. 177-189 (1987).

Zhang, L., et al., "Structure and Control Release of Chitosan/Carboxymethyl Cellulose Microcapsules", Journal of Applied Polymer Science, vol. 82, pp. 584-592 (2001).

Application and File History for U.S. Appl. No. 12/429,127, filed Apr. 23, 2009, inventors Myntti et al.

Application and File History for U.S. Appl. No. 14/324,889, filed Jul. 7, 2014, inventors Myntti et al.

\* cited by examiner

POLYSACCHARIDE PARTICLE MIXTURE

CROSS REFERENCE TO RELATED APPLICATIONS

This application is a continuation of application Ser. No. 14/324,889 filed Jul. 7, 2014, now allowed, which is a continuation of application Ser. No. 12/429,127 filed Apr. 23, 2009, now U.S. Pat. No. 8,802,652 B2, and which claims priority from U.S. Provisional Application Ser. No. 61/047,580 filed Apr. 24, 2008, the disclosures of each of which are incorporated herein by reference.

FIELD OF THE INVENTION

This invention relates to polysaccharides and to materials for use in the body.

BACKGROUND

Certain polysaccharide materials have been used for surgical repair or drug delivery. Documents relating to such materials include U.S. Pat. No. 5,820,608 (Luzio et al.), U.S. Pat. No. 5,993,846 (Friedman et al.), U.S. Pat. No. 6,123,965 (Jacob et al.), U.S. Pat. No. 6,342,251 B1 (lilum et al.), U.S. Pat. No. 6,706,690 B2 (Reich et al.), U.S. Pat. No. 6,835,389 B1 (Dohi et al.) and U.S. Pat. No. 7,195,675 B2 (Okazaki et al.); U.S. Patent Application Publication No. US 2005/0208122 A1 (Allen et al.); Published PCT Application No. WO 93/21906 A (Brown University Research Foundation) and Weng et al., *Rheological Characterization of in Situ Crosslinkable Hydrogels Formulated from Oxidized Dextran and N-Carboxyelhyl Chilosan*, Biomacromolecules, 8, 1109-1115 (2007). Polysaccharide gels may be used as tissue sealants in ear, nose and throat (ENT) procedures.

SUMMARY OF THE INVENTION

In order to avoid undue degradation during storage, it is desirable to package polysaccharide gel materials in dry form (e.g., as a powder or sponge) and rehydrate the material just prior to use. Rehydration sometimes presents difficulties. Some rehydrated materials provide gels or sponges with poor physical properties. The physical properties of a rehydrated gel may in some instances be improved via in situ crosslinking, but there may be an increased risk that an overly crosslinked gel will inadvertently be dislocated (e.g., aspirated) into the lungs or elsewhere in the form of large solid chunks. Some external crosslinking agents may damage tissue, or may cause residence times which are excessively long or difficult to control.

The present invention provides, in one aspect, a composition comprising free-flowing rehydratable particles of substantially collagen-free dehydrothermally crosslinked polysaccharide. In one exemplary embodiment the particles comprise a cellulose such as carboxymethylcellulose (CMC), and may provide a rehydrated gel having one or more desirable properties including rapid, clump-free rehydration; thixotropic behavior when sprayed or injected; high viscosity and cohesive gel character once in place; controllable biodegradation properties, resistance to premature biodegradation and an ability to break down or be dislocated without producing large solid chunks. In another exemplary embodiment the particles comprise a blend of CMC and chitosan, and may provide a rehydrated gel having one or more desirable properties like those provided by the disclosed CMC rehydrated gels, together with one or more additional desirable properties including inherent antimicrobial (e.g., bactericidal) behavior; hemostatic ability or the promotion of wound healing. The disclosed rehydrated gels may assist in returning an injured, inflamed or surgically repaired surface (e.g., a mucosal tissue surface) to a normal state, e.g., through one or more healing mechanisms such as modulation of an inflammatory response, phagocytosis, mucosal remodeling, reciliation or other full or partial restoration of normal function.

The invention provides in another aspect an implantable article comprising a rehydratable porous sponge comprising substantially collagen-free dehydrothermally crosslinked polysaccharide. The sponge may be packaged and sold in compressed form, may be trimmed to a desired size or shape for implantation at a treatment site, and may be rehydrated prior to or following implantation. Exemplary embodiments of the disclosed sponge include sponges made from CMC and sponges made from blends of CMC and chitosan.

The invention provides in another aspect a method for making a polysaccharide gel-forming composition, which method comprises providing a substantially collagen-free polysaccharide solution, drying the solution to form a powder, and dehydrothermally crosslinking the powder to form free-flowing particles that will provide a polysaccharide gel when rehydrated. Exemplary embodiments of the disclosed method include methods which make powders from CMC and from blends of CMC and chitosan.

The invention provides in another aspect a method for making an implantable article, which method comprises providing a substantially collagen-free polysaccharide solution, lyophilizing the solution to form a dried porous sponge, dehydrothermally crosslinking the sponge, and optionally compressing the sponge, thereby forming an implantable article which will form a polysaccharide sponge when rehydrated. Exemplary embodiments of this disclosed method include methods which make sponges from CMC and from blends of CMC and chitosan.

The invention provides in another aspect a method for treating tissue and other body structures, which method comprises applying thereto a gel or sponge comprising rehydrated substantially collagen-free dehydrothermally crosslinked polysaccharide.

Rehydration may present additional difficulties. Some dry powder materials are prone to clumping when combined with water. The clumps can be difficult to disperse and may plug syringes, cannula or spray nozzles. The invention provides, in yet another aspect, a method for converting a dry powdered composition to a gel, which method comprises dispersing free-flowing polysaccharide particles in a biocompatible water-miscible polar dispersant, and combining the resulting dispersion with sufficient aqueous solvent for the particles to convert them to a cohesive hydrogel. The polysaccharide particles may be crosslinked or uncrosslinked, and if crosslinked the crosslinking may be dehydrothermal crosslinking or crosslinking carried out using a separate crosslinking agent. The polysaccharide particles may be substantially collagen-free. The polysaccharide particles may be substantially a single polysaccharide or a blend of two or more polysaccharides. The cohesive hydrogel may be formed without visible clumps of unhydrated polysaccharide. The disclosed method may be followed by a treatment method including a step of injecting or spraying a layer of the cohesive hydrogel onto tissue (e.g., mucosal tissue) or other body structures.

BRIEF DESCRIPTION OF THE DRAWING

Like reference symbols in the various figures of the drawing indicate like elements. The elements in the drawing are not to scale.

DETAILED DESCRIPTION

Figure 1:
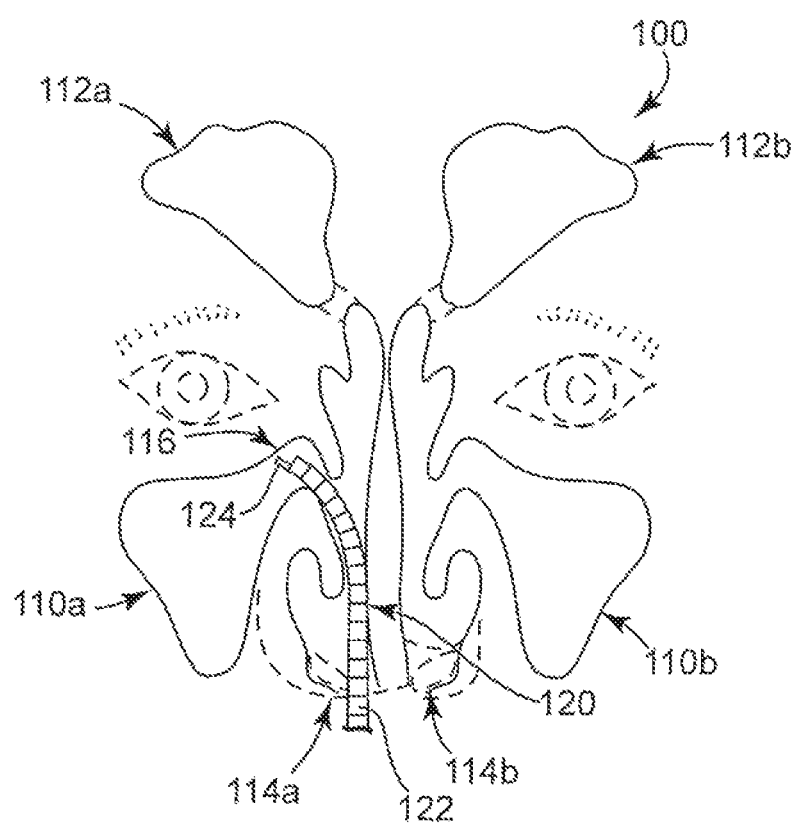
FIG. 1 is a schematic view showing the disclosed treatment method.

The following detailed description describes certain embodiments and is not to be taken in a limiting sense. All weights, amounts and ratios herein are by weight, unless otherwise specifically noted. The terms shown below have the following meanings:

The term "adhesion" refers to the sticking together of a body structure or prosthetic material to tissue, to the sticking together of tissue to tissue with which it is in intimate contact for extended periods, or to the formation of tissue that connects body structures, prosthetic materials or tissues to one another across a normally open space.

The term "antimicrobial" refers to an ability to cause greater than a 90% numeric reduction (viz., at least a 1-log order reduction) in a population of one or more of *Staphylococcus aureus, Pseudomonas aeruginosa, Streplococcus pneumonia, Haemophilus influenzae* or *Moraxella catarrhalis*.

The terms "attached" and "adhered" when used in reference to a bacterial biofilm and a surface mean that the biofilm is established on and at least partially coats or covers the surface, and has some resistance to removal from the surface. As the nature of this relationship is complex and poorly understood, no particular mechanism of attachment or adherence is intended by such usage.

The term "bacterial biofilm" means a community of bacteria attached to a surface, with the organisms in the community being contained within an extracellular polysaccharide (EPS) matrix produced by the bacteria.

The term "biocompatible" when used in reference to a substance means that the substance presents no significant deleterious or untoward effects upon the body.

The term "biodegradable" when used in reference to a substance means that the substance will degrade or erode in vivo to form smaller chemical or physical species. Such degradation process may be enzymatic, chemical or physical.

The term "bioresorbable" when used in reference to a substance means that the substance is capable of being absorbed by the body.

The term "cohesive" when used in reference to a liquid or gel means that the liquid or gel when placed on a level surface will tend to (but need not in all cases) stick to itself and form a unitary mass.

The term "comminuted" when used in reference to a particulate material means that the particles have been fractured and reduced in size by cutting, grinding, pulverizing, triturating or other particle fracturing process employing externally-applied force.

The term "conformal" when used in reference to a composition applied to tissue or other body structure means that the composition can form a substantially continuous layer over an area to which the composition has been applied.

The terms "detaching", "removing" and "disrupting" when used in reference to a bacterial biofilm attached or adhered to a surface mean that at least a significant amount of the biofilm initially present on the surface no longer is attached or adhered to the surface. No particular mechanism of detachment, removal or disruption is intended by such usage.

The term "fluid" when used in reference to a substance means that the substance is a liquid having a loss modulus (G") greater than its storage modulus (G') and a loss tangent (tan δ) greater than 1.

The term "gel" when used in reference to a substance means that the substance is deformable (viz., is not a solid), G" is less than G' and tan δ is less than 1.

The term "gelation" when used with respect to formation of a gel layer means the time at which G" equals G' and tan δ equals 1.

The term "hemostat" means a device or material which stops blood flow.

The term "hydrogel" when used in reference to a gel means that the gel is hydrophilic and contains water.

The term "hydrated" when used in reference to a device or substance means that the device or substance contains uniformly distributed chemically-bound water. A "fully hydrated" device or substance is incapable of taking up additional water of hydration. A "partially hydrated" device or substance is capable of taking up additional water of hydration.

The term "inner ear" means the semicircular canals and cochlea.

The term "middle ear" means the region defined by the tympanic membrane, interior structures such as the ossicular chain, the surrounding lining and bordering structures such as the mastoid.

The term "mucoadhesive" when used in reference to a device or substance means that the device or substance will adhere to the mucus covering epithelia.

The term "nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx.

The term "polysaccharide" includes derivatives of polysaccharides and modified polysaccharides, as well as derivatives of individual polysaccharide species and modified individual polysaccharide species. For example, the term "carboxymethylcellulose" includes carboxymethylcellulose derivatives and modified carboxymethylcelluloses, the term "chitosan" includes chitosan derivatives and modified chitosans, and the term "starch" includes starch derivatives and modified starches.

The term "protective" when used in reference to a layer of a composition atop tissue or other body structure means that the layer may assist in returning an injured, inflamed or surgically repaired tissue surface to a normal state, e.g., through one or more healing mechanisms such as modulation of an inflammatory response, phagocytosis, mucosal remodeling, reciliation or other full or partial restoration of normal function.

The term "residence time" when used in reference to a protective gel layer atop tissue or other body structure means the time period during which the gel layer or portion thereof remains in place in vivo under gross observation.

The term "solvating" means to form a solution or dispersion containing a solvent or other carrier within which a solute is dissolved or suspended.

The term "substantially collagen-free" means containing a sufficiently low amount of collagen so as not to pose a potential risk of transmission of or infection with bovine spongiform encephalopathy (BSE) or variant Creutzfeldt-Jakob disease (vCJD).

The term "thin" when used in reference to a protective layer atop tissue or other body structure means having an average thickness less than about two millimeters.

Referring to FIG. 1, the disclosed treatment method may be performed for example in the nasal or sinus cavities 100 of a patient, including the maxillary sinuses 110a, 110b and frontal sinuses 112a, 112b, which may be accessed through nares 114a, 114b. It should be noted that external features of the patient, including nares 114s, 114b, are shown in dashed lines. When the patient suffers for example from chronic rhinosinusitis, one or more treatment sites such as treatment site 116 associated with a surface of maxillary sinus 110O may be medically or if need be surgically addressed. Treatment site 116 includes ciliated epithelium of maxillary sinus 110a and may include an associated layer of bacteria inhabiting an associated biofilm (not shown in FIG. 1). The treatment site need not be limited to natural tissue and may include an artificial structure (not shown in FIG. 1) such as a sinus packing or stent which may also be covered at least in part with a layer of bacterial biofilm. If present, the biofilm may be removed using a solvating system (for example, the solvating system described in U.S. Patent Application Publication No. US 2007/0264310 A1) which may be applied to treatment site 116 using an introducer 120 with an articulatable delivery tube 122 containing an irrigation duct (hidden in FIG. 1) through which the solvating system may flow to a nozzle 124 at the distal end of introducer 122 and thence to the treatment site. The solvating system and residues of the biofilm may be removed from the treatment site via an aspiration duct (hidden in FIG. 1). The disclosed rehydrated gel composition may likewise be applied at the treatment site using the same or a different irrigation duct in introducer 120. Those skilled in the art will appreciate that the rehydrated gel (and if used, the solvating system) may be applied to the treatment site using other methods or devices. Exemplary other methods include power spray or other spray application, lavage, misting, mopping, wicking, dripping and trephination and exemplary other devices include spray nozzles (e.g., single component or multiple component spraying nozzles) and syringes (e.g., single barrel or multiple barrel glass or plastic syringes and bulb syringes). The treatment method may also be performed in other parts of the body. The treatment method has particular utility in non-vascular applications, including treatment of tissues (e.g., mucosal tissues) or structures in or near the ears, nose or throat and openings, recesses, passageways or joints in the limbs or spinal column.

Figure 2:
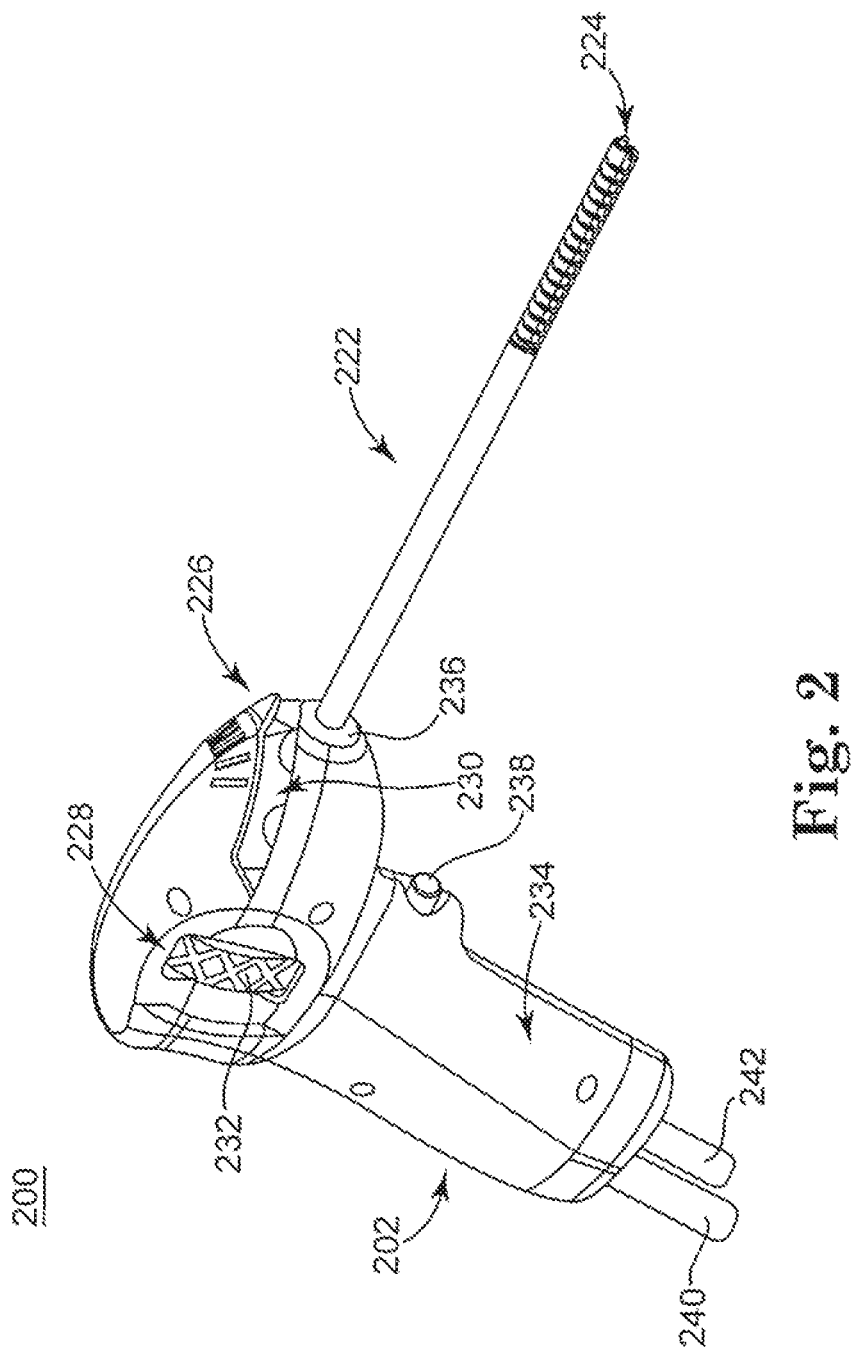
FIG. 2 is a perspective view of a dispensing instrument which may be used in the disclosed treatment method.

FIG. 2 shows an exemplary instrument 200 which may be used in the disclosed treatment method. Instrument 200 includes a handle 202 and an introducer 222 whose distal end 224 (referenced generally) includes a spray nozzle, irrigation and aspiration ducts (not separately numbered in FIG. 2). Instrument 200 can optionally further include a first actuator assembly 226 (referenced generally) and a second actuator assembly 228 (referenced generally). A control wheel 230 in first actuator assembly 226 may be operable by a user to effectuate bending of the introducer 222, and a control wheel 232 in second actuator assembly 228 may be operable by a user to effectuate movement or rotation relative to introducer 222 of liquid sprayed from distal end 224 of introducer 222. Handle 202 serves generally as a housing for various other components of instrument 200 and as a support for introducer 222. Handle 202 may have a pistol grip-like shape, defining a grip portion 234 and a nose 236. Grip portion 234 is sized and shaped for grasping by a user's hand, whereas nose 236 is adapted for connection to introducer 222. Trigger 238 and an associated sensor and valve (not shown in FIG. 2) may be used to control the flow of the disclosed rehydrated gel (and if used, the disclosed solvating system) through irrigation tubing 240 and thence through the spray nozzle in distal end 224 and onto the desired treatment site. Trigger 238 may be provided with a multidirectional range of motion and associated with one or more additional sensors and valves (not shown in FIG. 2) to control removal from a treatment site of the solvating system, biofilm residue and other debris through the aspiration duct in distal end 224 and thence to aspiration tubing 242. Trigger 238 may also be used to control the flow of the disclosed rehydrated gel through a separate lumen in irrigation tubing 240 and thence through the spray nozzle in distal end 224 and onto the desired treatment site.

Figure 3:
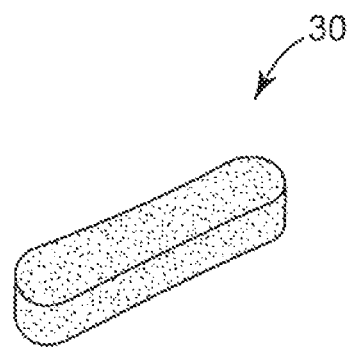
FIG. 3 is a perspective view of the disclosed sponge.
Figure 4:
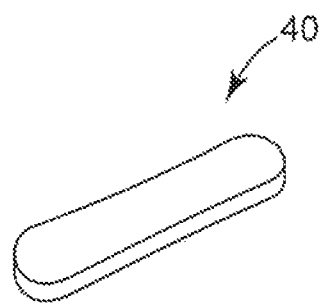
FIG. 4 is a perspective view of the disclosed sponge in a compressed state.

The applied rehydrated gel may fill the treatment site (e.g., a nasal or sinus cavity, or an opening, recess, passageway or joint in a portion of the limbs or spinal column), in which case the disclosed gel layer may be very thick and not exposed to air or other nearby gases, and with differing thicknesses throughout the layer. The disclosed rehydrated gel may also be applied as a thin film or other conformal coating in which case the disclosed gel layer may be relatively thin and exposed to air or other nearby gases, and with a substantially uniform thickness throughout the layer. The rehydrated gel composition provides a protective layer which may be viscous, elastic or viscoelastic. The protective layer desirably adheres to mucosal or other natural tissues (e.g., cartilage or bone) at the treatment site and resists detachment or other disruption until natural degradation or resorption of the gel layer takes place, e.g., after a residence time in vivo of from one day to a few (e.g., 2, 3 or 4) days, weeks or months. Meanwhile bacterial recolonization or reinfection may be significantly reduced or prevented, and improved healing and reciliation may take place. The protective gel layer may provide various therapeutic advantages including but not limited to bacterial adhesion repellence, anti-infective properties, local immune modulation, tissue protection, reduction or elimination of pain or bleeding, reduction in inflammation, optimization of environment for ciliary regrowth, reduction in adhesions to critical anatomy, and the like. These advantages may arise due to a variety of mechanisms including a) killing bacteria, b) inhibiting bacterial colonization, c) inhibiting the adherence of bacteria to tissue, d) reducing tissue morbidity or abscess formation, e) reducing or preventing disease recurrence (for example, specifically reducing the chronic inflammation related to bacterial toxin and EPS), f) coating and protecting tissue during healing, such as by maintenance of a moist wound which promotes platelet aggregation, or by closure of a dry wound without excessive scabrous formation, g) hemostasis, h) optimizing the environment for reciliation of the mucosa, i) speeding the growth or regrowth of cilia and j) delivering therapeutic agent(s) to the treatment site. Desirably the protective gel layer will adhere to a portion of the mucosa while leaving the cilia in unadhered portions free to undergo natural rhythmic cilia motion (viz., cilia beating), will if desired also deliver antimicrobial agents or additional therapeutic agents, and desirably will discourage or prevent bacteria from adhering to the treatment site.

FIG. 3 shows an example 30 of the disclosed sponge in an uncompressed state, and FIG. 4 shows an example 40 of the disclosed sponge in a compressed state. In its uncompressed form prior to rehydration, sponge 30 provides an essentially anhydrous porous polysaccharide matrix. A compressed sponge such as sponge 40 may be formed before or after dehydrothermal crosslinking, using a variety of techniques including a press with opposing platens, calendaring rollers, a plastic bag subjected to external air pressure or internal vacuum, and other compression techniques that may be envisioned by persons having ordinary skill in the art. Either the compressed or uncompressed forms of the disclosed sponge may be employed in medical procedures. Before placing a sponge such as sponge 30 or sponge 40 in a treatment site, the sponge may be trimmed to a desired size or shape (using, for example, a suitable punch and die if trimming is done at a manufacturing site, or scissors or a scalpel if trimming is done at the time of placement). The untrimmed or trimmed sponge may then be rehydrated. If previously compressed, the sponge may be allowed to expand before, during or after insertion into the treatment site. The emplaced sponge may provide various therapeutic advantages like those described above in connection with the protective gel layer.

A wide variety of polysaccharides may be employed in the disclosed rehydratable gel composition and in the disclosed sponge. In addition to celluloses and chitosans, exemplary polysaccharides include agars, alginates, carrageenans, chitins, chondroitin sulfates, dextrans, galactomannans, glycogens, hyaluronic acids, starches and other biocompatible polysaccharides capable of being formed into a hydrogel or self-supporting sponge. Derivatives (including oxidized polysaccharides and salts) and mixtures of polysaccharides (including derivatives) may also be used. Compositions containing mixtures of polysaccharides are especially desirable in order to form hydrogels and sponges whose properties would not be provided using a single polysaccharide. For example compositions containing CMC and chitosan provide an especially desirable set of properties. Other desirable compositions include those containing chitosan together with an alginate, hyaluronic acid or chondroitin sulfate. The chosen polysaccharide(s) desirably can be crosslinked via a dehydrothermal condensation reaction as described in more detail below, and one or all of the polysaccharides in a mixture of polysaccharides may be so crosslinked. The chosen polysaccharide(s) also desirably are water soluble or may be rendered so, e.g., by suitable acidification.

A variety of celluloses may be employed in the disclosed rehydratable gel and in the disclosed sponge, including CMC, methylcellulose, ethylcellulose, hydroxypropyl cellulose, hydroxypropyl methyl cellulose and hemicellulose, as well as derivatives thereof including oxidized celluloses. Exemplary cellulosic materials may be obtained from a variety of commercial sources including Dow Wolff Cellulosics (for example, the WALOCEL™ CRT line of sodium carboxymethylcellulose products), Hercules, Inc. (for example, the AQUALON™ line of cellulose gum and carboxymethylcellulose products) and Sigma-Aldrich Co. (for example, No. C4021 microgranular cellulose). The cellulosic material desirably is obtained in particulate form, for example, as free-flowing granules whose average particle diameter is less than about 1 mm, less than about 100 μm, about 1 to about 80 μm, or less than 1 μm.

A variety of chitosans may be employed in the disclosed rehydratable gel and in the disclosed sponge. Exemplary unmodified chitosans and their salts (including citrate, nitrate, lactate, phosphate, chloride and glutamate salts) may be obtained from a variety of commercial sources including KitoZyme S. A., Fluka Chemie AG, the NovaMatrix unit of FMC BioPolymer AS and Sigma-Aldrich Co. Chitosan may also be synthesized by deacetylation of chitin (poly-N-acetyl-D-glucosamine) to eliminate acetyl groups on the nitrogen atom by hydrolysis. The resulting polymer has a plurality of repeating units (e.g., about 30 to about 3000 repeating units, about 60 to about 600 repeating units, or such other amount as may be desired for the chosen end use) some or all of which contain deacetylated amino groups (e.g., about 30 to about 100% or about 60 to about 95% of the total repeating units), with the remaining repeating units (if any) containing acetylated amino groups. The polymer is cationic and may be regarded as being composed from glucosamine monomers. The chitosan may have a variety of number average molecular weights, e.g., about 5 to about 2000 kDa, about 10 to about 500 kDa, or about 10 to about 100 kDa. The chitosan may for example be an ultralow molecular weight material having a number average molecular weight less than about 50 kDa, a low molecular weight material having a number average molecular weight of about 50 to about 200 kDa, a medium molecular weight material having a number average molecular weight of about 200 to about 500 kDa or a high molecular weight material having a number average molecular weight greater than about 500 kDa. Chitosan derivatives may also be employed, for example derivatives in which one or more hydroxyl or amino groups have been modified for the purpose of altering the solubility or mucoadhesion characteristics of the derivative. Exemplary derivatives include thiolated chitosans, and non-thiolated chitosan derivatives such as acetylated, alkylated or sulfonated chitosans (for example O-alkyl ethers, O-acyl esters, cationized trimethyl chitosans and chitosans modified with polyethylene glycol). Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolated reactant, e.g., as described in Published PCT Application No. WO 03/020771 A1 and in Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004), Krauland et al., *Viscoelastic Properties of a New in situ Gelling Thiolated Chitosan Conjugate*, Drug Development And Industrial Pharmacy, 31, 885-893 (2005), Bernkop-Schnürch, *Thiomers: A new generation of mucoadhesive polymers*, Advanced Drug Delivery Reviews, 57, 1569-1582 (2005) and Bernkop-Schnürch et al., *Thiomers: Preparation and in vitro evaluation of a mucoadhesive nanoparticulate drug delivery system*, International journal of Pharmaceutics, 317, 76-81 (2006). The chitosan desirably is obtained in particulate form, for example, as free-flowing granules whose average particle diameter is less than about 1 mm, less than about 100 μm, about 1 to about 80 m, or less than 1 μm.

Sources for and types of other polysaccharides (for example, agars, alginates, carrageenans, chitins, chondroitin sulfates, dextrans, galactomannans, glycogens, hyaluronic acids, starches) may be chosen by persons skilled in the art based on selection characteristics similar to those given above for celluloses and chitosans. When combined in a mixture, the amounts of each polysaccharide may be varied widely to attain a desired combination of properties. For example, by altering the ratio of two polysaccharides in a blend, the biodegradable or bioresorbable characteristics and residence time of the blend may be altered. A mixture of two polysaccharides may for example contain about 99 to about 1% of the first polysaccharide and about 1 to about 99% of the second polysaccharide, or about 80 to about 20% of the first polysaccharide and about 20 to about 80% of the second polysaccharide, or about 60 to about 40% of the first polysaccharide and about 40 to about 60% of the second polysaccharide. Through appropriate selection of the types and amounts of polysaccharides in a mixture, rehydratable gels and sponges with tunable properties may be obtained. For example, a blend of CMC and chitosan may have good bacteriostatic performance due to the chitosan and controlled, sustained and tunable degradation rates due to the CMC, whereas chitosan used alone may form a gel or sponge having inherently poor mechanical and resorbtive properties and CMC used alone may form a gel or sponge lacking bactericidal properties.

The disclosed rehydratable gel composition and sponge are substantially collagen-free. Desirably the rehydratable gel composition and sponge are sufficiently free of collagen (e.g., containing no collagen at all) so as to be saleable worldwide for use without restriction in humans.

The disclosed rehydratable gel composition and sponge optionally are crosslinked before being packaged and sent to end users. Crosslinking preferably is carried out using a dehydrothermal crosslinking process. For the disclosed rehydratable gel this preferably is done by dehydrothermally crosslinking a mass of free-flowing rehydratable polysaccharide particles to form free-flowing rehydratable crosslinked polysaccharide particles. In other words, the particles preferably are themselves individually crosslinked while still remaining free-flowing and capable of later rapid dissolution and rehydration. For the disclosed sponge, crosslinking preferably is done by dehydrothermally crosslinking a shaped porous article which has been made by placing a solution of the desired polysaccharide in a suitable mold and lyophilizing the solution to form a porous solid having a shape corresponding to the desired uncompressed sponge shape. In other words, the sponge preferably is shaped and made porous prior to crosslinking.

Dehydrothermal crosslinking is in effect a solid state crosslinking process in which a material is exposed to one or both of heat and reduced pressure to cause initial dehydration followed by loss of additional water and formation of crosslinking bonds via an inter- or intra-molecular condensation process. It is not necessary to add external crosslinking agents, and in the case of the disclosed particles the presence of such agents could make it difficult to retain their free-flowing nature. Dehydrothermal crosslinking desirably involves dehydrating the product to be crosslinked to a moisture content less than about 1%, and using sufficient additional heat or vacuum to achieve a desired crosslink density. For example, in the absence of vacuum, temperatures above about 80° C., above about 90° C., above about 100° C. or above about 120° C. may be employed, with higher temperatures generally providing faster reaction rates. The polysaccharide desirably is not heated to an extent sufficient to cause browning, and accordingly temperatures less than 160° C. or less than 150° C. are preferred. Fairly long heating times may be needed at ambient pressure, for example, about 40 hours at 140-150° C. plus about total 20 hours for warmup and cooldown. When reduced pressure is used, lower temperatures may be employed and a pressure of at most about 1 mm Hg, and preferably at most about $10^{-3}$ mm Hg may be preferred. Thus the higher the temperature, the lower the required vacuum or beating time required to arrive at a given crosslink density, and vice versa. It is accordingly difficult to specify an exact heating time or range of heating times, although times of at least about 10 hours, at least about 20 hours, at least about 30 hours or about 40 to about 60 hours (not counting the times required for warmup and cooldown) may be employed. In many cases it will suffice to determine the heating time, temperature and pressure empirically, for example by using the Gel Retention Time test shown in the Examples to evaluate whether an appropriate degree of crosslinking has been obtained. For an uncrosslinked sample, the Gel Retention Time may for example be 1 day or less, whereas by using an appropriate degree of dehydrothermal crosslinking the Gel Retention Time may for example be extended to at least 2 days and preferably about 3 to about 7 days. The uncrosslinked sample may also tend to rehydrate less rapidly, absorb more water or form a more viscous gel or paste than its dehydrothermally crosslinked counterpart. In comparison to a conventionally crosslinked material ground into powder form, dehydrothermally crosslinked particles may be non-comminuted, may be crosslinked due to a condensation reaction (e.g., a dehydration reaction leading to the loss of water, or a reaction leading to the loss of another small molecule such as hydrogen chloride, methanol or acetic acid) rather than due to other crosslinking reactions (e.g., reactions involving addition polymerization (e.g. of vinyl groups), ionic reactions, or reactions involving sulfide or amine groups). In comparison to a conventionally crosslinked material ground into powder form, dehydrothermally crosslinked particles may also have a narrower polydispersity index, lower number average molecular weight, the capability to undergo further crosslinking, lower production costs and lower manufacturing capital requirements.

When two or more polysaccharides are employed to make the disclosed rehydratable gel, the dehydrothermal crosslinking process may be performed on one or on more than one of the polysaccharides before the particles have been blended. This permits customization of properties such as gelation behavior, gelation time and degradation time following implantation, by varying properties including the crosslinking time, temperature or vacuum for each polysaccharide component followed by blending of the crosslinked (or if desired, uncrosslinked) components after completion of the dehydrothermal crosslinking reaction(s) on the individual blend components. If desired, the resulting blend may be subjected to an additional dehydrothermal crosslinking reaction. The particles could also be kept separate and later mixed by an end user, although this will normally be less convenient than forming the mixture at a manufacturing site.

Dehydrothermal crosslinking conditions for the disclosed sponges are similar to those which may be employed for the polysaccharide particles. When two or more polysaccharides are employed to make the disclosed sponge, a mixture of the polysaccharides may be formed in solution, lyophilized and dehydrothermally crosslinked. As another approach, one or more of the polysaccharides in such a mixture may be dehydrothermally crosslinked, and the remaining polysaccharide(s) in such mixture may be imbibed into the dehydrothermally crosslinked polymer and the resulting swelled article may be lyophilized to form a sponge. These and other related approaches can permit differing degrees of property customization.

The disclosed rehydratable gel composition and sponge typically will be subjected to sterilization and placed in suitable sealed packaging (for example, a syringe, vial or bag made of a suitable material) prior to shipment to an end user. Additional property customization may be carried out by using a sterilization procedure such as gamma radiation or electron beam (E-Beam) processing to cause controlled chain scission. Cold ionizing radiation sterilization (e.g., cold E-Beam sterilization) may be employed to limit the degree of chain scission, as discussed in International Application No. PCT/US2009/041593 (corresponding to International Publication No. WO 2009/132229 A2), filed even date herewith.

The disclosed rehydratable gel composition and sponge may be rehydrated prior to placement or insertion in a treatment site, or may be placed while in a dry state and then rehydrated in silu (e.g., via the addition of an externally-supplied rehydrating fluid, by the uptake of endogenous fluids, or both). Rehydrating the sponge normally is relatively straightforward, and may be carried out by immersing or saturating the sponge with water or an aqueous solution containing any other desired ingredients. For example, normal saline solution may be a preferred and readily available rehydration solution, and other materials such as phosphate buffered saline (PBS) may be used if desired. Rehydrating the rehydratable gel particles may as noted above present additional difficulties due to the tendency of some dry powdered materials to form clumps when combined with water. Clumping may however be avoided by dispersing the rehydratable gel particles in a biocompatible water-miscible polar dispersant, followed by mixing the dispersion with sufficient aqueous particle solvent (viz., a water-based solvent for the particles) to convert the particles to a cohesive hydrogel. The dispersant is a thus a sufficiently poor solvent for the particles so that the mixture of particles and dispersant will not form a true solution. The particles in such a dispersion desirably are sufficiently small so that the dispersion is stable or quasi-stable (e.g., a colloidal dispersion or a reasonably persistent suspension) after the particles and dispersant have been agitated, e.g., by swirling them together. Without being bound by theory, the addition of the aqueous particle solvent is believed to permit rehydration to occur approximately simultaneously at the surface of each suspended particle via dissolution of the surrounding dispersant into the aqueous particle solvent phase, thereby permitting formation of a cohesive hydrogel without forming visible clumps of unhydrated polysaccharide. In this fashion a dispersed polysaccharide may be combined with water or an aqueous solution to form a clump-free hydrogel even though the dry powdered polysaccharide would not ordinarily do so. In many instances the disclosed method may be used to prepare a satisfactory clump-free gel using passage between two syringes, mild agitation or other simple mixing techniques without requiring the use of a mechanical stirrer. The disclosed mixing method may also permit formation of very concentrated hydrogels which could not be obtained by merely mixing a powdered polysaccharide with water or acidified water. The polysaccharide concentration typically will depend on the chosen molecular weight, and may for example be about 1 to about 20%, about 1 to about 10% or about 1 to about 5% of the rehydrated gel. The gel may desirably form in less than 30 minutes, less than 20 minutes, less than 10 minutes, less than 5 minutes, less than 1 minute or even essentially immediately after rehydration. For polysaccharides which do not immediately rehydrate, it may be desirable to saturate the powder and inject it before the polysaccharide has become too viscous to spray or otherwise dispense through a small orifice.

The selection of dispersant and aqueous particle solvent may depend upon the chosen polysaccharide. For polysaccharides such as chitosan which have relatively poor solubility in pure water but which become soluble when the water is acidified, deionized water may be used as the dispersant and acidified water may be used as the aqueous particle solvent. Other combinations of dispersant and aqueous solvent may also be used. For example, ethanol, isopropanol or acetone may be used as the dispersant for many polysaccharides (including chitosan and blends containing chitosan) and deionized water, normal saline solution or PBS may be used as the aqueous particle solvent.

The disclosed rehydratable gel particles may as noted above be crosslinked or uncrosslinked, and if crosslinked the crosslinking may be dehydrothermal crosslinking or crosslinking carried out using a separate crosslinking agent (for example, genipin, oxidized polysaccharide or glutaraldehyde). When crosslinked using a separate crosslinking agent, the resulting polymer may optionally be lyophilized and if need be comminuted to provide free-flowing particles.

The disclosed rehydratable gel composition and sponge may optionally include a variety of other ingredients before or after rehydration. Exemplary other ingredients include other solvents, acids, bases, buffering agents, antimicrobial agents, therapeutic agents and other adjuvants. An acid, base or buffering agent may for example maintain the gel at an appropriate pH for contacting human tissue, e.g., a pH greater than 5, a near-neutral pH, or a pH less than 8.5. Exemplary buffering agents include barbitone sodium, glycinamide, glycine, potassium chloride, potassium phosphate, potassium hydrogen phthalate, sodium acetate, sodium citrate, sodium phosphate and their conjugate acids.

The disclosed rehydratable gel composition and sponge desirably are inherently antimicrobial without requiring addition of a separate antimicrobial agent. A separate antimicrobial agent may be employed if desired. A useful list of such antimicrobial agents may be found, for example, in the above-mentioned U.S. Patent Application Publication No. US 2007/0264310 A1.

Exemplary therapeutic agents which may be employed in the disclosed rehydratable gel composition and sponge include any material suitable for use at the intended treatment site including analgesics, anti-cholinergics, anti-fungal agents, antihistamines, steroidal or non-steroidal anti-inflammatory agents, anti-parasitic agents, antiviral agents, biostatic compositions, chemotherapeutic/antineoplastic agents, cytokines, decongestants, hemostatic agents (e.g., thrombin), immunosuppressors, mucolytics, nucleic acids, peptides, proteins, steroids, vasoconstrictors, vitamins, mixtures thereof, and other therapeutic materials that will be known to those skilled in the art. A useful list of such therapeutic agents may be found, for example, in the above-mentioned U.S. Patent Application Publication No. US 2007/0264310 A1.

Other adjuvants that may be included in the disclosed rehydratable gel composition and sponge include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be known to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and theology modifiers including thickeners and thixotropes. The disclosed rehydratable gel composition and sponge desirably do not contain ingredients which might potentially harm patient tissues or structures, e.g., mucosal tissues in the nasal or sinus cavities.

In those instances where it is desirable to remove water from tissue, e.g., to remove fluid from polyps or edematous tissue, a hyperosmolar agent may be employed in the disclosed rehydratable gel composition and sponge. Exemplary hyperosmolar agents include furosemide, sodium chloride gel and other salt preparations that draw water from tissue or substances which directly or indirectly change the osmolar content of the mucous layer. Where sustained release or delayed release of a therapeutic agent is desirable, a release agent modifier may also be included.

The disclosed rehydratable gel composition and sponge may desirably be used as a part of a multi-step treatment regimen which disrupts a bacterial biofilm and discourages its return. For example, a series of steps that may be broadly classified as Cleansing/Disrupting, Killing, Aerating, Protecting/Coating, and Healing may be carried out. The Cleansing/Disrupting step may be carried out by administering a solvating system as discussed above in connection with FIG. 1 and FIG. 2. The Killing step may be carried out by applying a suitable antimicrobial agent to the treatment site. This may for example be accomplished by including an antimicrobial agent in the solvating system, as a separately-applied composition, or in both the solvating system and in a separately-applied composition. An antimicrobial agent may also be applied or administered post operatively. The Aerating step may be carried out by providing air passageways or improving air passageways to the treated tissues by opening occluded or partially occluded passages, e.g., the sinuses or sinus ostia for nasal applications. This may for example be accomplished by surgically removing obstructive tissue structures or by manually displacing such structures. The Protecting/Coating step may be carried out by coating at least part of the thus-treated tissue with the disclosed gel composition or by covering at least part of the thus-treated tissue with the disclosed sponge. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal function. The multi-step treatment regimen may include or be followed by a Clearing step in which the gel composition or sponge is sufficiently biodegradable or bioresorbable to disappear from the treatment site in a desired time period, e.g., more than 1 day, more than 3 days, or about 4 to 7 days, and desirably without shedding large solid chunks. The disclosed method may advantageously be accomplished without requiring surgery, for example by applying and removing the optional solvating system through normal aspiration/suction techniques or by simple flushing of affected tissue followed by application of the disclosed gel composition or sponge. A comparable series of steps may be performed in a multi-step treatment regimen in a portion of the middle or inner ear. Further details regarding such a regimen may be found in U.S. Patent Application Publication No. US 2007/0264310 A1.

The invention is further illustrated in the following non-limiting examples.

Example 1

Dehydrothermally Crosslinked CMC

Powdered sodium carboxymethylcellulose (CMC 52MSC from Emerging Technologies, Inc.) was combined with 1% titanium dioxide and dehydrothermally crosslinked by warming to 140° C. over 10 hours, heating at 150-160° C. for 40 hours, and cooling to ambient temperature over 10 hours. A free-flowing, white powder with an average particle diameter of about 40 μm was obtained. The powder was packaged in 1.5 gram portions in polyurethane pouches and E-Beam sterilized at 30 kGy.

Example 2

Syringe Rehydration and Dispensing

A 0.7 g portion of the Example 1 CMC powder was combined with 3 mL deionized water in a 10 mL LUER-LOK™ syringe (from Becton, Dickinson and Co.). The syringe was connected to a second such 10 mL syringe using a LUER™ connector (from Becton, Dickinson and Co.) and the syringe plungers were alternately depressed in an effort to rehydrate the powder. A poorly-mixed mass containing many clumps was obtained, and the clumps occluded the passage between the syringes. In a second run, a 0.7 g portion of the Example 1 CMC powder was combined with 0.5 mL ethanol and shaken, resulting in an apparently stable suspension. A 3 mL portion of deionized water in the second syringe was added to the suspension and then the syringe plungers were alternately depressed to mix the ingredients, resulting in the gradual formation of a clear, homogenous hydrogel which was completely free of visible unhydrated CMC particles. The hydrogel could readily be injected through a 2.7 mm inside diameter, 10 cm long cannula onto a target surface, resulting in a thick, highly viscous uniform gel with no noticeable clumps. The gel looked somewhat like an amorphously-shaped sponge.

Example 3

Adhesion

Samples of the Example 2 gel were placed between collagen-coated pins in an MTS tensile testing machine (MTS Systems Corp.), and evaluated at a separation rate of 25.4 mm/min to determine tensile adhesive strength for the gel-collagen bond. A value of about 55 kPa was obtained, whereas only about 35 kPa was obtained using a gel made with uncrosslinked CMC powder.

Example 4

Gel Retention Time

A 1.5 g portion of the Example 1 powder was rehydrated to form a clump-free gel using the method of Example 2. The gel was submerged in 200 mL PBS, then poured onto a 150 μm sieve, allowed to drain and weighed. The gel was returned to the collected PBS solution, stored overnight and the sieve and reweighing procedure repeated for a total of three times at which point the gel had disappeared. The resulting 3 day test duration was recorded as the Gel Retention Time. A gel made from the Example 1 CMC powder without dehydrothermal crosslinking had a Gel Retention Time of less than 1 day.

Example 5

Chitosan Suspensions and Gels

Figure 5:
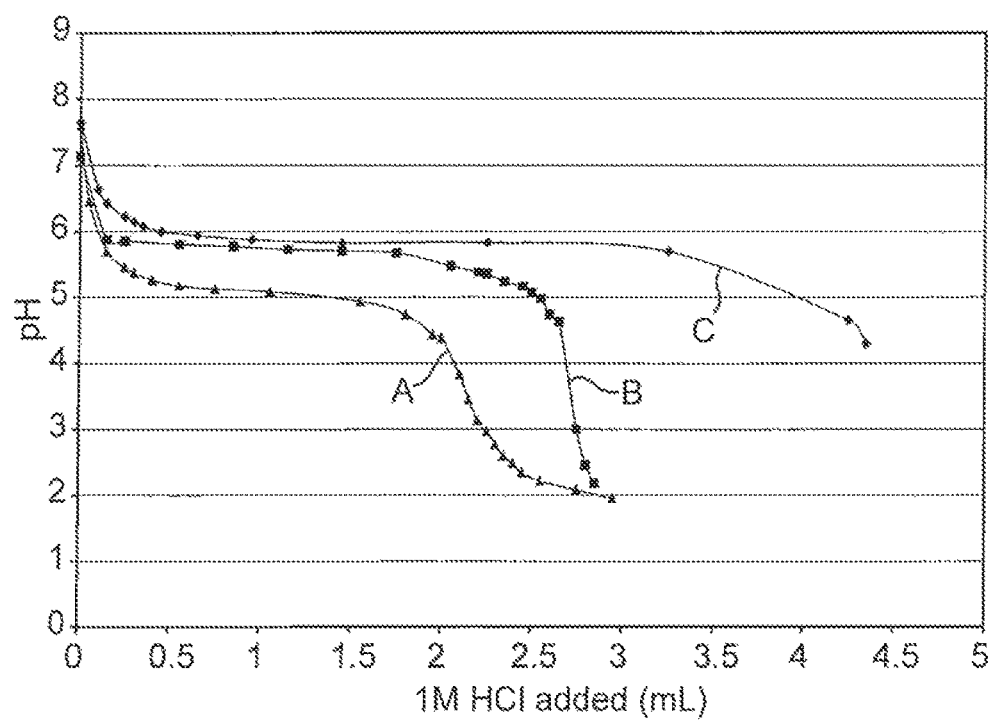
FIG. 5 is a graph showing acid titration of three chitosan suspensions.

High molecular weight powdered chitosan obtained from crab shells (BIOCHEMICA™ high viscosity chitosan from Sigma-Aldrich Co.) was suspended in deionized water at addition levels of 10, 25 and 50 g/L. A stirred 50 mL portion of each suspension was titrated with 1M HCl. As shown in FIG. 5, where the 10, 25 and 50 g/L suspensions are respectively identified as curves A, B and C, the pH value decreased gradually with the addition of acid. The pH value passed through an inflection point at about pH 6 and less than 1 mL of acid addition, corresponding to the start of noticeable gel formation. High viscosity gels were obtained by the time the pH value passed through another inflection point, at approximately pH 4.5 and at about 2, 3 or 5 mL of acid addition for curves A, B and C, respectively. At yet lower pH values the chitosan had by then become fully hydrated and the additional acid further acidified the water and diluted the gel.

In a separate run, a 1% solution of the high molecular weight chitosan was formed by adding the chitosan powder to deionized water containing 1% acetic acid. The solution had a 453 cP viscosity when evaluated at 37° C. using a BROOKFIELD™ DV-II+ Pro cone and plate viscometer equipped with a CP-52 cone spindle. A similarly-prepared 1% solution of low molecular weight chitosan (BIO-CHEMICA low viscosity chitosan from Sigma-Aldrich Co.) had a 185 cP viscosity.

Example 6

Dehydrothermally Crosslinked Chitosan Adhesion

Figure 6:
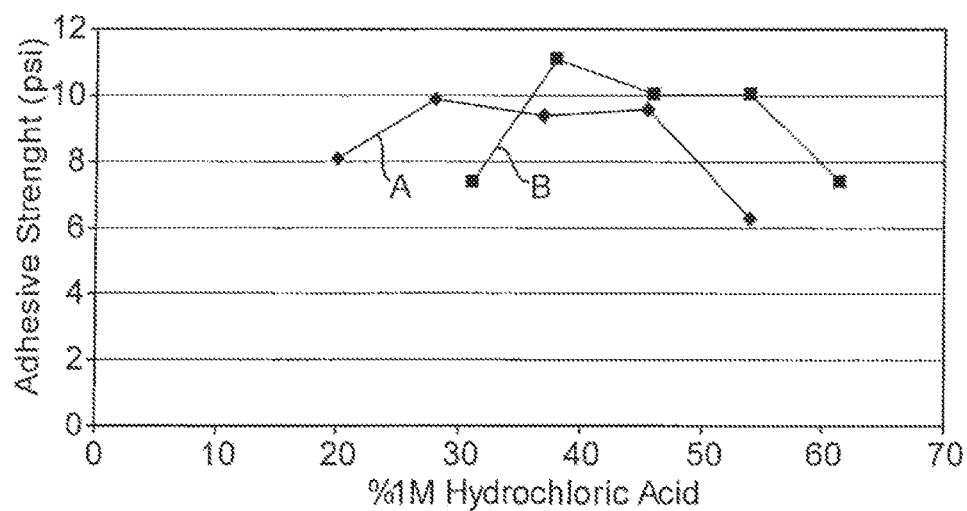
FIG. 6 and FIG. 7 are plots showing adhesion results for chitosan gels dehydrothermally crosslinked at 90° C. and 120° C.
Figure 7:
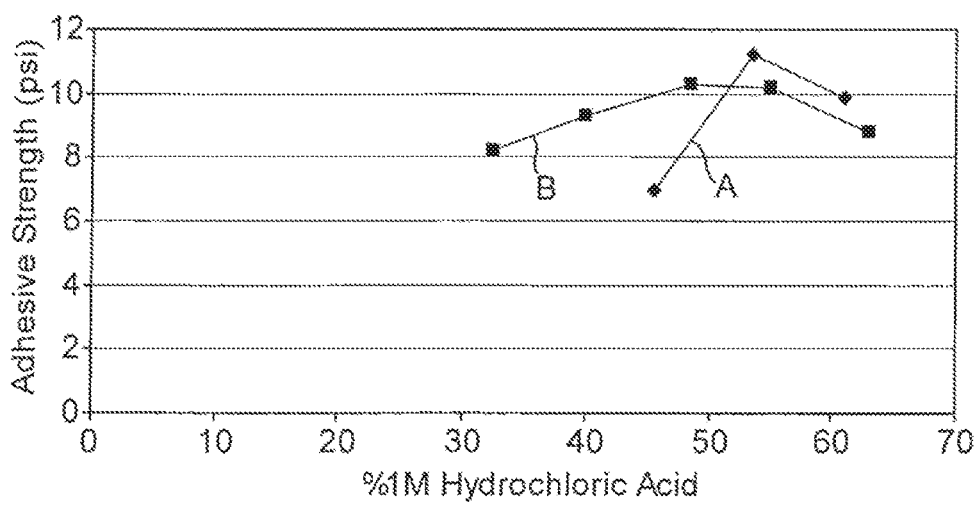

Using the method of Example 1, low and high molecular weight powdered chitosan was dehydrothermally cross-linked at 90° C. for 10 hours or at 120° C. for 20 hours, added to varying amounts of 1M HCl to form gels and evaluated for adhesion using the method of Example 3. FIG. 6 shows the adhesion results for chitosan crosslinked at 90° C. and FIG. 7 shows the adhesion results for chitosan crosslinked at 120° C.

In a separate run, medium molecular weight chitosan was dehydrothermally crosslinked at 120° C. for 40 hours using the method of Example 1 and evaluated for adhesion using the method of Example 2. A value of about 65 kPa was obtained, whereas only about 41 kPa was obtained using a gel made with uncrosslinked CMC powder.

Example 7

Polysaccharide Blends

In a series of runs, powdered chitosan (ultralow molecular weight chitosan oligosaccharide lactate, or BIO-CHEMICA™ low or medium viscosity crab shell chitosan, all from Sigma-Aldrich Co.) was employed by itself, in a blend of chitosans, or in a blend with the Example 1 powdered CMC, and mixed with water acidified with varying amounts of HCl or acetic acid. The resulting mixtures were stirred for five minutes using a powered stirrer. Doing so enabled the antimicrobial testing described below, but would be much less convenient if required to be performed prior to surgery. The stirred solutions were evaluated to determine the antimicrobial activity of the resulting gels versus *E. Coli, S. Aureus, P. Aeruginosa* and in some instances *S. Pneumoniae*. The antimicrobial activity evaluation used a modified zone of inhibition plate procedure, in which a small quantity of the gel was streaked across agar plates which had been freshly streaked with the desired microbe. Unlike a traditional zone of inhibition test, in which an antibiotic-soaked paper disk is placed against the agar surface and the antibiotic diffuses outwardly through the agar, the viscous nature of the gel discouraged such diffusion. The results were thus somewhat Boolean in nature, and mainly provided an indication as to whether or not inhibition had occurred. The results are shown below in Table 1.

TABLE 1

Antimicrobial Activity Evaluation

| Run No. | Chitosan (amount and type) | CMC (amount) | Acidification[1] | E. Coli | S. Aureus | P. Aeruginosa | S. Pneumoniae |
|---|---|---|---|---|---|---|---|
| 1 | 100% LMW[2] | | pH 4.5 | Yes | Yes | Yes | |
| 2 | 100% LMW | | pH 6 | No | Mild | No | |
| 3 | 100% MMW[3] | | pH 4.5 | No | No | No | |
| 4 | 100% MMW | | pH 6 | No | Mild | No | |
| 5 | 20% LMW | 80% | pH 4.5 | Yes | Yes | Yes | |
| 6[4] | 20% LMW | 80% | pH 4.5 | Yes | Yes | Yes | |
| 7 | 40% LMW | 60% | pH 4.5 | Yes | Yes | Yes | |
| 8 | 60% LMW | 40% | pH 4.5 | Yes | Yes | Yes | |
| 9 | 80% LMW | 20% | pH 4.5 | Yes | Yes | Yes | |
| 10[4] | 80% LMW | 20% | pH 4.5 | Yes | Yes | Yes | |
| 11 | 20% LMW | 80% | pH 5 | Yes | Yes | Yes | |
| 12 | 40% LMW | 60% | pH 5 | Yes | Yes | Yes | |
| 13 | 60% LMW | 40% | pH 5 | Yes | Yes | Yes | |
| 14 | 80% LMW | 20% | pH 5 | Yes | Yes | Yes | |
| 15 | 20% LMW | 80% | pH 5.5 | Yes | Yes | Yes | |
| 16 | 40% LMW | 60% | pH 5.5 | Yes | Yes | Yes | |
| 17 | 60% LMW | 40% | pH 5.5 | Yes | Yes | Yes | |
| 18 | 80% LMW | 20% | pH 5.5 | Yes | Yes | Yes | |
| 19 | 20% LMW | 80% | 0.1% acetic acid | Yes | Yes | Yes | Yes |
| 20 | 20% LMW | 80% | 0.12% acetic acid | Yes | Yes | Yes | Yes |
| 21 | 20% LMW | 80% | 0.14% acetic acid | Yes | Yes | Yes | Yes |
| 22 | 20% LMW | 80% | 0.16% acetic acid | Yes | Yes | Yes | Yes |
| 23 | 20% LMW | 80% | 0.18% acetic acid | Yes | Yes | Yes | Yes |
| 24 | 20% LMW | 80% | 0.2% acetic acid | Yes | Yes | Yes | Yes |
| 25 | 20% LMW | 80% | 0.2% acetic acid | Yes | Yes | Yes | Yes |
| 26 | 20% LMW | 80% | 0.2% acetic acid | No | No | No | No |
| 27 | 50% LMW | 50% | 0.2% acetic acid | Yes | Yes | Yes | Yes |

TABLE 1-continued

Antimicrobial Activity Evaluation

| Run No. | Chitosan (amount and type) | CMC (amount) | Acidification[1] | Microbial Inhibition | | | |
|---|---|---|---|---|---|---|---|
| | | | | E. Coli | S. Aureus | P. Aeruginosa | S. Pneumoniae |
| 28 | 20% LMW + 75% MMW | 5% | 0.2% acetic acid | Yes | Yes | Yes | Yes |
| 29 | 20% LMW + 80% MMW | | pH 5 | Yes | Yes | Yes | |
| 30 | 10% LMW + 90% MMW | | pH 5 | Yes | Yes | Yes | |
| 31 | 5% LMW + 95% MMW | | pH 5 | Yes | Yes | Yes | |
| 32 | 3% LMW + 97% MMW | | pH 5 | Yes | Yes | Yes | |
| 33 | 2% LMW + 98% MMW | | pH 5 | Yes | Yes | Yes | |
| 34 | 1% LMW + 99% MMW | | pH 5 | Yes | Yes | Yes | |
| 35 | 0.5% LMW + 99.5% MMW | | pH 5 | Yes | Yes | Yes | |
| 36 | 100% MMW | | pH 5 | Yes | Yes | Yes | |
| 37 | 100% ULMW[5] | | pH 5 | Yes | Yes | Yes | Yes |

[1]The indicated pH values are the pH at the start of rehydration, as obtained using HCl. Where acidification was performed using acetic acid, the amount of added acid is shown.
[2]"LMW" is low molecular weight chitosan.
[3]"MMW" is medium molecular weigh chitosan.
[4]Gel sample aged 48 hours prior to microbial inhibition test.
[5]"ULMW" is ultralow molecular weigh chitosan.

The results in Table 1 show that chitosan and blends of chitosan with the polysaccharide carboxymethylcellulose may be rehydrated to provide gel layers with inherent antimicrobial properties.

Example 8

A free-flowing crosslinked powder may be prepared by dissolving a dry powdered polysaccharide polymer such as carboxymethyl chitosan in water to produce a viscous solution containing about 5 wt. % polymer. A crosslinker solution containing 10 wt. % dialdehyde starch or 0.1 wt. % glutaraldehyde may be quickly mixed with the polymer solution by placing each solution in a 10 mL LUER-LOK™ syringe (from Becton, Dickinson and Co.), connecting the syringes to one another using a LUER™ connector (from Becton, Dickinson and Co.) and alternately depressing the syringe plungers to exchange the fluids between the two syringes several times. After a short dwell period during which crosslinking takes place, a cohesive gel should be obtained. The gel may be converted to particles by freezing and lyophilize the frozen gel, followed by grinding the lyophilization product.

Example 9

A free-flowing crosslinked powder may also be prepared by soaking a dry powdered polysaccharide polymer in a nonsolvating liquid crosslinking agent or nonsolvating crosslinker solution. The dry powdered carboxymethyl chitosan starting material used in Example 8 may be soaked in ethylene glycol diglycidyl ether (e.g., E27203 ethylene glycol diglycidyl ether from Sigma-Aldrich) for sufficient time to permit crosslinking to occur. The resulting mass of free-flowing, crosslinked particles may be washed with methanol to remove residual crosslinking agent and dried using gentle heat. Depending on the chosen polysaccharide, a variety of crosslinkers may be employed. For example, ethylene glycol diglycidyl ether may be replaced with hexamethylene diglycidyl ether or other glycidyl crosslinker reactive towards hydroxyl or amine groups. If the polysaccharide contains primary amine groups, appropriately reactive crosslinkers such as dialdehyde starch, oxidized methyl cellulose or glutaraldehyde may be employed.

Example 10

Equal volumes of a 2.5 wt. % solution of carboxymethyl chitosan in PBS and 10 wt. % dialdehyde starch were quickly mixed using two 3 mL syringes like the 10 mL syringes described in Example 8. The resulting cohesive hydrogel was expelled from the back of the syringes to provide a mass that maintains its shape.

Example 11

Equal volumes of a 5 wt. % solution of carboxymethyl chitosan in PBS were crosslinked via E-beam radiation both when frozen and at room temperature. The resulting hydrogels were lyophilized into readily powderable sponges. When placed in PBS, the sponges persisted for three to seven days.

In addition to a composition comprising free-flowing rehydratable particles of substantially collagen-free dehydrothermally crosslinked polysaccharide, other embodiments of the invention include like compositions:
  wherein the particles contain substantially a single polysaccharide;
  wherein the particles comprise a mixture of polysaccharides;
  wherein the polysaccharide comprises cellulose, chitosan, agar, alginate, carrageenan, chitin, chondroitin sulfate, dextran, galactomannan, glycogen, hyaluronic acid, starch or mixture thereof,
  wherein the polysaccharide comprises an oxidized polysaccharide or salt;

wherein the polysaccharide comprises carboxymethylcellulose;
wherein the polysaccharide is substantially only carboxymethylcellulose;
wherein the polysaccharide comprises chitosan;
wherein such chitosan is unmodified;
wherein the polysaccharide comprises a mixture of chitosan and another polysaccharide;
wherein the polysaccharide comprises a mixture of carboxymethylcellulose and chitosan; or
further comprising a sealed syringe with which the particles can be rehydrated and dispensed.

In addition to an implantable article comprising a rehydratable porous sponge comprising substantially collagen-free dehydrothermally crosslinked polysaccharide; other embodiments of the invention include like articles:
wherein the polysaccharide is substantially a single polysaccharide;
wherein the polysaccharide comprises a mixture of polysaccharides;
wherein the polysaccharide comprises cellulose, chitosan, agar, alginate, carrageenan, chitin, chondroitin sulfate, dextran, galactomannan, glycogen, hyaluronic acid, starch or mixture thereof;
wherein the polysaccharide comprises an oxidized polysaccharide or salt;
wherein the polysaccharide comprises carboxymethylcellulose;
wherein the polysaccharide is substantially only carboxymethylcellulose;
wherein the polysaccharide comprises chitosan;
wherein such chitosan is unmodified;
wherein the polysaccharide comprises a mixture of chitosan and another polysaccharide;
wherein the polysaccharide comprises a mixture of carboxymethylcellulose and chitosan; or
wherein the sponge is compressed and may be trimmed to a desired size or shape, rehydrated and allowed to expand after rehydration.

In addition to a method for making a polysaccharide gel-forming composition, which method comprises:
a) providing a substantially collagen-free polysaccharide solution;
b) drying the solution to form a powder, and
c) dehydrothermally crosslinking the powder to form free-flowing particles that will provide a polysaccharide gel when rehydrated,
other embodiments of the invention include like methods:
wherein the particles contain substantially a single polysaccharide;
wherein the polysaccharide comprises a mixture of polysaccharides;
wherein the polysaccharide comprises cellulose, chitosan, agar, alginate, carrageenan, chitin, chondroitin sulfate, dextran, galactomannan, glycogen, hyaluronic acid, starch or mixture thereof;
wherein the polysaccharide comprises an oxidized polysaccharide or salt;
wherein the polysaccharide comprises carboxymethylcellulose;
wherein the polysaccharide is substantially only carboxymethylcellulose;
wherein the polysaccharide comprises chitosan;
wherein such chitosan is unmodified;
wherein the polysaccharide comprises a mixture of chitosan and another polysaccharide;
wherein the polysaccharide comprises a mixture of carboxymethylcellulose and chitosan; or
further comprising packaging the particles in a sealed syringe with which the particles can be rehydrated and dispensed.

In addition to a method for making an implantable article, which method comprises:
a) providing a substantially collagen-free polysaccharide solution,
b) lyophilizing the solution to form a dried porous sponge, and
c) dehydrothermally crosslinking the sponge,
thereby forming an implantable article which will form a polysaccharide sponge when rehydrated,
other embodiments of the invention include like methods:
wherein the sponge contains substantially a single polysaccharide;
wherein the sponge contains a mixture of polysaccharides;
wherein the polysaccharide comprises cellulose, chitosan, agar, alginate, carrageenan, chitin, chondroitin sulfate, dextran, galactomannan, glycogen, hyaluronic acid, starch or mixture thereof;
wherein the polysaccharide comprises an oxidized polysaccharide or salt;
wherein the polysaccharide comprises carboxymethylcellulose;
wherein the polysaccharide is substantially only carboxymethylcellulose;
wherein the polysaccharide comprises chitosan;
wherein such chitosan is unmodified;
wherein the polysaccharide comprises a mixture of chitosan and another polysaccharide;
wherein the polysaccharide comprises a mixture of carboxymethylcellulose and chitosan;
further comprising compressing the dried porous sponge before or after dehydrothermal crosslinking; or
further comprising packaging the implantable article in a sealed container.

In addition to a method for treating mucosal tissue and other body structures, which method comprises applying thereto a gel or sponge comprising rehydrated substantially collagen-free dehydrothermally crosslinked polysaccharide, other embodiments of the invention include like methods:
comprising placing the gel or sponge in a nasal or sinus cavity;
comprising placing the gel or sponge in a middle or inner ear;
comprising placing the gel or sponge in an opening, recess, passageway or joint in a limb;
comprising placing the gel or sponge in an opening, recess, passageway or joint in a spinal column;
comprising spraying the gel;
further comprising trimming the sponge to a desired size or shape, rehydrating the trimmed sponge and allowing it to expand;
wherein the wherein the polysaccharide is substantially a single polysaccharide;
wherein the polysaccharide comprises a mixture of polysaccharides;
wherein the polysaccharide comprises cellulose, chitosan, agar, alginate, carrageenan, chitin, chondroitin sulfate, dextran, galactomannan, glycogen, hyaluronic acid, starch or mixture thereof,
wherein the polysaccharide comprises an oxidized polysaccharide or salt;

wherein the polysaccharide comprises carboxymethylcellulose;
wherein the polysaccharide is substantially only carboxymethylcellulose;
wherein the polysaccharide comprises chitosan;
wherein such chitosan is unmodified;
wherein the polysaccharide comprises a mixture of chitosan and another polysaccharide; or
wherein the polysaccharide comprises a mixture of carboxymethylcellulose and chitosan.

In addition to a method for converting a dry powdered composition to a gel, which method comprises:
a) dispersing free-flowing polysaccharide particles in a biocompatible water-miscible polar dispersant, and
b) combining the resulting dispersion with sufficient aqueous solvent for the particles to convert them to a cohesive hydrogel, other embodiments of the invention include like methods:
wherein the water-miscible polar dispersant is water and the aqueous solvent for the particles is acidified water;
wherein the water-miscible polar dispersant comprises ethanol;
wherein the water-miscible polar dispersant comprises isopropanol or acetone;
wherein the polysaccharide particles have been crosslinked;
wherein the polysaccharide particles have been dehydrothermally crosslinked;
wherein the polysaccharide particles have been crosslinked using a separate crosslinking agent;
wherein the polysaccharide particles are uncrosslinked;
wherein the polysaccharide particles are substantially collagen-free;
wherein the polysaccharide particles are substantially a single polysaccharide;
wherein the polysaccharide particles are a blend of two or more polysaccharides;
wherein the polysaccharide comprises cellulose, chitosan, agar, alginate, carrageenan, chitin, chondroitin sulfate, dextran, galactomannan, glycogen, hyaluronic acid, starch or mixture thereof,
wherein the polysaccharide comprises an oxidized polysaccharide or salt;
wherein the polysaccharide comprises carboxymethylcellulose;
wherein the polysaccharide is substantially only carboxymethylcellulose;
wherein the polysaccharide comprises chitosan;
wherein such chitosan is unmodified;
wherein the polysaccharide comprises a mixture of chitosan and another polysaccharide;
wherein the polysaccharide comprises a mixture of carboxymethylcellulose and chitosan;
comprising forming the cohesive hydrogel without visible clumps of unhydrated polysaccharide;
further comprising injecting or spraying a layer of the cohesive hydrogel onto mucosal tissue;
further comprising injecting or spraying the cohesive hydrogel into an opening, recess, passageway or joint in a limb; or
further comprising injecting or spraying the cohesive hydrogel into an opening, recess, passageway or joint in a spinal column.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

The invention claimed is:

1. A composition comprising a dry, free-flowing, sterilized mixture of separate rehydratable particles comprising about 20 to about 95 wt. % of chitosan particles containing amino groups and about 80 to about 5 wt. % of oxidized polysaccharide particles containing aldehyde groups in sealed packaging, wherein the amino group functionality and molecular weight of the chitosan and the aldehyde group and molecular weight of the oxidized polysaccharide are such that the mixture of chitosan particles and separate oxidized polysaccharide particles are rehydratable in situ when removed from the sealed packaging and applied in a dry state to a surgical tissue site or wound moistened with bodily fluids such that the mixture of chitosan particles and separate oxidized polysaccharide particles will adhere to such tissue site or wound and will adhere to one another by inter-particle crosslinking reaction of amino groups on the chitosan particles with aldehyde groups on the polysaccharide particles, wherein the dry, free-flowing, sterilized mixture of chitosan and oxidized polysaccharide particles contains less than 10% wt. % water.

2. A composition according to claim 1 wherein the chitosan particles have a number average molecular weight of about 10 to about 500 kDa.

3. A composition according to claim 1 wherein the oxidized polysaccharide particles comprise oxidized starch particles.

4. A composition according to claim 1 wherein the mixture contains about 80 to about 20% of the chitosan particles and about 20 to about 80% of the oxidized polysaccharide particles.

5. A composition according to claim 1 wherein the mixture contains about 60 to about 40% of the chitosan particles and about 40 to about 60% of the oxidized polysaccharide particles.

6. A composition according to claim 1 wherein the mixture contains about 60 to about 40% of the chitosan particles and about 40 to about 60% of oxidized starch particles.

7. A composition according to claim 1 wherein the chitosan particles and oxidized polysaccharide particles are non-comminuted.

8. A composition according to claim 1 wherein the chitosan particles and-oxidized polysaccharide particles in the sealed packaging are uncrosslinked.

9. A composition according to claim 1 wherein the chitosan particles and oxidized polysaccharide particles are rehydratable in situ to form a gel on the tissue site or wound.

10. A composition according to claim 9 wherein the chitosan particles and oxidized polysaccharide particles provide a polysaccharide gel when rehydrated.

11. A composition according to claim 1 wherein the chitosan particles and oxidized polysaccharide particles contain a sufficiently low amount of collagen so as not to pose a potential risk of transmission of or infection with bovine spongiform encephalopathy (BSE) or variant Creutzfeldt-Jakob disease (vCJD).

12. A composition according to claim 1 wherein the dry, free-flowing, sterilized mixture of chitosan and oxidized polysaccharide particles are capable of forming a substantially continuous conformal protective layer over such tissue.

13. A composition according to claim 12 wherein the tissue comprises mucosal tissue.

14. A composition according to claim 13 wherein the mucosal tissue is in a nasal cavity.

15. A composition according to claim 13 wherein the mucosal tissue is in a sinus cavity.

16. A composition according to claim 12 wherein the tissue comprises an injured, inflamed or surgically repaired surface and the mixture assists in returning such injured, inflamed or surgically repaired surface to a normal state.

17. A composition according to claim 16 wherein the return of such surface to a normal state includes reciliation.

18. A composition according to claim 1 further comprising a sustained release therapeutic agent.

19. A composition according to claim 1 wherein the mixture of particles is inherently antimicrobial without requiring addition of a separate antimicrobial agent.

* * * * *